United States Patent [19]

Madou et al.

[11] Patent Number: 4,874,500
[45] Date of Patent: Oct. 17, 1989

[54] MICROELECTROCHEMICAL SENSOR AND SENSOR ARRAY

[75] Inventors: Marc J. Madou, Palo Alto; Takaaki Otagawa, Fremont, both of Calif.

[73] Assignee: SRI International, Menlo Park, Calif.

[21] Appl. No.: 73,805

[22] Filed: Jul. 15, 1987

[51] Int. Cl.⁴ ............................................. G01N 27/30
[52] U.S. Cl. ................................... 204/412; 204/408; 204/416; 357/25
[58] Field of Search ............... 204/408, 412, 416, 406; 357/25

[56] References Cited

U.S. PATENT DOCUMENTS

| | | | |
|---|---|---|---|
| 3,663,409 | 5/1972 | Greene | 204/408 |
| 4,020,830 | 5/1977 | Johnson et al. | |
| 4,062,750 | 12/1977 | Butler | 204/15 X |
| 4,214,968 | 7/1980 | Battaglia et al. | |
| 4,225,410 | 9/1980 | Pace | 204/412 |
| 4,259,164 | 3/1981 | Rasch et al. | |
| 4,269,682 | 5/1981 | Yano et al. | |
| 4,340,457 | 7/1982 | Kater | |
| 4,419,211 | 12/1983 | Brauer | 204/408 |
| 4,455,213 | 6/1984 | Neti et al. | 204/415 |
| 4,457,161 | 7/1984 | Iwanaga et al. | 73/23 |
| 4,487,679 | 12/1984 | Stare | 204/418 |
| 4,502,938 | 3/1985 | Covington et al. | 204/412 |
| 4,528,085 | 7/1985 | Kitajima et al. | 204/416 |
| 4,534,825 | 8/1985 | Koning et al. | 156/644 |
| 4,542,640 | 9/1985 | Clifford | 73/23 |
| 4,549,951 | 10/1985 | Knudson et al. | 204/416 |
| 4,556,474 | 12/1985 | Pierson | 204/416 |
| 4,562,723 | 1/1986 | Hubner | 73/23 |
| 4,571,293 | 2/1986 | Seshimoto et al. | 204/418 |
| 4,586,143 | 4/1986 | Kaneyasu et al. | 364/509 |
| 4,592,824 | 6/1986 | Smith et al. | 204/416 |
| 4,713,165 | 12/1987 | Conover et al. | 204/403 |

OTHER PUBLICATIONS

Y. Miyahara et al., Micro Enzyme Sensors Using Semiconductor and Enzyme Immobilization Techniques.

Primary Examiner—G. L. Kaplan
Attorney, Agent, or Firm—Fliesler, Dubb, Meyer & Lovejoy

[57] ABSTRACT

The invention relates to a microelectrochemical electrode structure comprising a monolithic substrate having a front surface and a back surface facing generally away from one another, a first well extending into the substrate from the surface towards the back surface and ending in a first well bottom, and a first passage extending into the substrate from the back surface to the first well bottom. A first electrode is located wholly within the first well. A first conductor in the first passage serves for electrically communicating the first electrode to adjacent the back surface. A plurality of such electrode structures can be provided on a single substrate. The use of semiconductor processing technology allows the entire sensor to be extremely small. If desired, an integrated circuit can be provided on the back surface of the substrate for amplifying or otherwise processing signals from the first electrode. Analysis can be carried out for vapors or dissolved species (ionic or non-ionic).

54 Claims, 5 Drawing Sheets

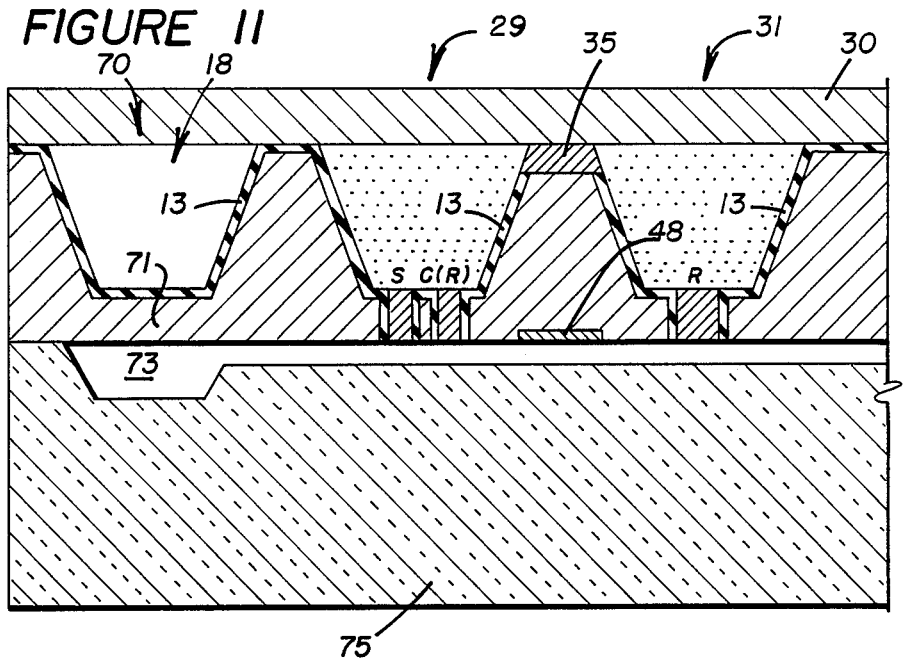
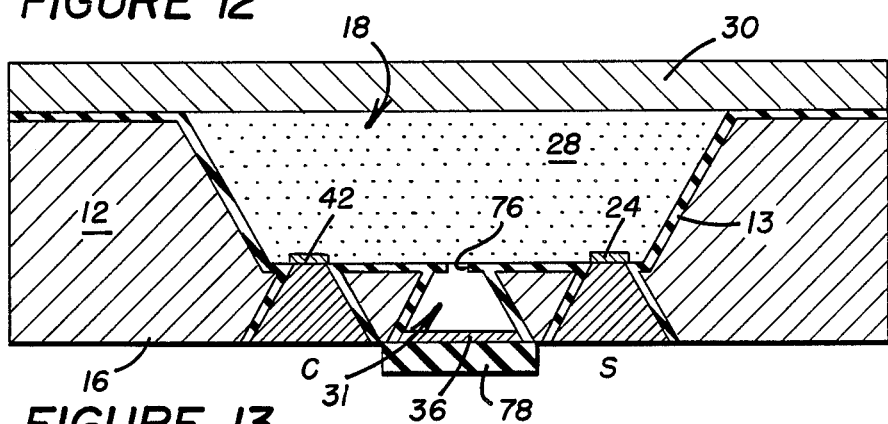
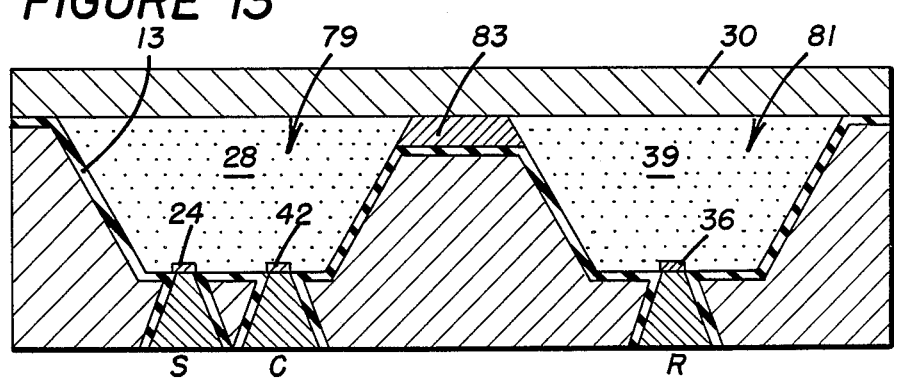

MICROELECTROCHEMICAL SENSOR AND SENSOR ARRAY

TECHNICAL FIELD

The present invention relates to micro-electrochemical sensors useful for detecting various chemicals, including vaporous and gaseous species and dissolved species, in very low concentrations. The micro-electrochemical sensors themselves are formulated by integrated circuit (IC) engineering techniques and can be extremely small in size, namely, as small as one-fifth to one-sixth the size of the smallest previously known sensors. Among numerous other uses, they may be utilized to analyze blood chemistry, in vivo.

BACKGROUND ART

In a large number of situations it is desirable to be able to analyze a sample, be it a liquid sample or a gaseous sample, for one or more constituents. Often, it is desirable to analyze for several constituents at once. For example, it is desirable to be able to analyze blood for such diverse components as $H^+$, $K^+$, $CO_2$ and $O_2$, etc. It is also often desirable to be able to analyze air samples for air borne contaminants such as CO, NO, $NO_2$, $N_2O$, $SO_2$, $H_2S$ and $O_2$ and other gases as well.

Within the last several years a number of sensors have been developed based upon one or more of the techniques developed by integrated circuit engineering technology. For example, U.S. Pat. No. 4,020,830, issued May 3, 1977 to C. C. Johnson, et al, utilizes a chemical sensitive field-effect transistor (FET) transducer for selectively detecting and measuring chemical properties of substances to which the transducer is exposed. Basically, the chemical being detected interacts with certain substances to modulate the electric field produced in the substrate semiconductor material between diffusion regions thereof. Such FET devices have been demonstrated to be useable for detecting ions as well as gases, and indirectly certain dissolved molecules. However, fluctuations in drain current leading to errors are still a significant problem. These fluctuations can be associated with thermal noise or they can be light induced. Layers that make the FET chemically sensitive and selective are very difficult to deposit on the gates of such devices, especially since often several layers of different composition are needed. All of this leads to errors or makes fabrication difficult. Still further, reference electrodes are very difficult to implement in FET structures.

S. J. Pace, as set forth in U.S. Pat. No. 4,225,410, discloses a disposable integrated miniaturized array of chemical sensors for analyzing concurrently a number of analytes in a fluid sample. Each sensor of the array is a complete electrochemical cell having its own reference and indicator electrodes and is selective with respect to a particular analyte. The sensors are all formed on top of the surface of a substrate which is prepared by press forming powdered alumina with appropriate through holes and imprints for the electrochemical circuit. Because of the manufacturing techniques such sensors and sensor arrays must be relatively large and are more properly describable as minisensors rather than microsensors.

In U.S. Pat. No. 4,549,951, issued Oct. 29, 1985 to M. B. Knudson, et al, a relatively large, compared to both of the devices discussed above, ion selective electrode is set forth which is used along with a separate reference electrode. The ion-selective membrane of the electrode sits on a conductor embedded in a plastic substrate. This is basically a small ion-selective electrode with the membrane sitting on top of a conductor and without an internal reference electrolyte or true reference electrode. Further, construction of such an electrode design in micro sizes appears to be beyond the current state of the art.

In the devices of U.S. Pat. Nos. 4,020,830, 4,225,410, and 4,549,951 the entire electrochemical cell sits upon the surface of a substrate. This leads to a significant problem in providing proper encapsulation. In the case of U.S. Pat. No. 4,020,830, all of the electronic circuitry is included on the analyte detecting side of the FET. This leads to problems between the chemicals and the electronic circuitry which are either in contact with one another or closely adjacent to one another.

The prior art, including the above discussed patents, does not yet provide microelectrochemical sensors and sensor arrays incorporating both amperometric and potentiometric elements, which operate at room temperature and consume little power, which provide versatile, multi-purpose-multi-channel, real time monitoring of vapors, gases, molecules and ions, which are micro-portable and field rugged, which have fast response times at ambient temperature, which are free of interferences from such parameters as oxygen deficiency and humidity, which can be produced inexpensively using sophisticated modern micro-fabrication technologies, which have high specificity and high selectivity, for example, parts-per-billion level detection of such gases CO, NO, $NO_2$, $H_2S$, $SO_2$, and $N_2H_4$ and parts-per-million detection of such gases as HCN, $Cl_2$, $H_2$, $O_2$, $C_2H_5OH$, HCHO, $C_3H_3N$, $O_3$, $C_2H_2$, $C_2H_4$, $CH_4$, $C_2H_6$, $C_3H_8$, and organophosphate vapors, and which are adaptable for detecting ionic electroactive species in parts-per-billion in solutions, including, for example, $Cl^-$, $Br^-$, $I^-$, $SCN^-$, $CN^-$, $S_2O_3^{2-}$, $OCl^-$, $SO_3^{2-}$, phenols, aromatic amines, nitro compounds, organoarsines, and metal ions, e.g., $Cu^{2+}$, $Fe^{3+}$.

The present invention is directed to solving one or more of the problems as set forth above.

DISCLOSURE OF INVENTION

In one embodiment of the present invention a microelectrochemical electrode structure is set forth. The aforementioned electrode structure comprises a monolithic substrate having a front surface and a back surface facing generally away from one another. A first well extends into the substrate from the front surface towards the back surface and ends in a first well bottom. A first passage extends into the substrate from the back surface to the first well bottom. A first electrolytic cell including a first electrode is located wholly between the front and back surfaces of the substrate. A first conductor is located in the first passage and electrically communicates the first electrode to adjacent the back surface.

In accordance with one embodiment of the invention an electrolytic medium is in the first well. A barrier covers the first well, the barrier having an outfacing surface and an infacing surface. The infacing surface is in flow contact with the electrolytic medium. The barrier provides entry into the electrolytic medium of a selected moiety in response to contact of a selected species with the outfacing surface. The barrier is at least substantially impermeable to the electrolytic medium.

Another embodiment of the present invention is a sensor array including a plurality of such first electrode structures in the substrate.

Optionally, each electrode structure can have more than one electrode in the first well.

An electrode structure in accordance with the present invention is characterized by extremely small size, is operable at room temperature, utilizes low power, is field rugged, has a fast response time, is not sensitive to interferences due to oxygen deficiency or differences in humidity, can be readily mass produced using sophisticated microfabrication technologies, has high specificity and high selectivity, can have very short signal lines to signal amplification circuitry integrated and embedded in the back side of the substrate thereby providing a high signal-to-noise ratio, and is useful in accordance with specific embodiments to detect vapors, dissolved ions and dissolved nonionic species (including dissolved gases). The structure is also very well suited to having a pressure element incorporated in an array therewith. Because the geometric configuration of a resistive or capacitive sensor is so similar to the structure created for the chemical sensitive elements it only requires a few more processing steps to also include a pressure element on the same substrate. In some applications (e.g., biomedical) such added features are very beneficial.

In accordance with embodiments of the present invention a single substrate can have an array of one or more electrode structures, each sensitive for one or several of a number of different chemical species. And, the entire sensor array can be so small that it can be readily positioned in, for example, a catheter in the blood stream and can be used to give a constant readout of such chemicals as $CO_2$, $O_2$, $K^+$, $H^+$, and the like. In accordance with certain embodiments of the present invention it is possible to include integrated circuitry electronics on the back surface of the substrate removed from the electrochemistry whereby one can amplify the signals and/or obtain electrical output signals which are specifically indictive of the concentration of one or of a number of species. The electrode structure of the present invention can be designed to exhibit substantially Nernstian slopes for ionic species. The amperometric electrode structures of the present invention can be designed to exhibit substantially linear dependency on concentration. The bottom of the first well can be chosen to be at different distances from the front and back surfaces of the substrate for different intended applications.

BRIEF DESCRIPTION OF THE DRAWINGS

The invention will be better understood by reference to the figures of the drawings wherein like numbers denote like parts throughout and wherein:

FIG. 11 illustrates a side sectional view of a portion of FIG. 10 and shows the combination of an array of sensor elements with a pressure sensor;

FIG. 12 illustrates, in similar view to FIG. 1, an alternate embodiment of the present invention;

FIG. 13 illustrates, in similar view to FIG. 1, an alternate embodiment of the present invention.

BEST MODE FOR CARRYING OUT INVENTION

Figure 1:
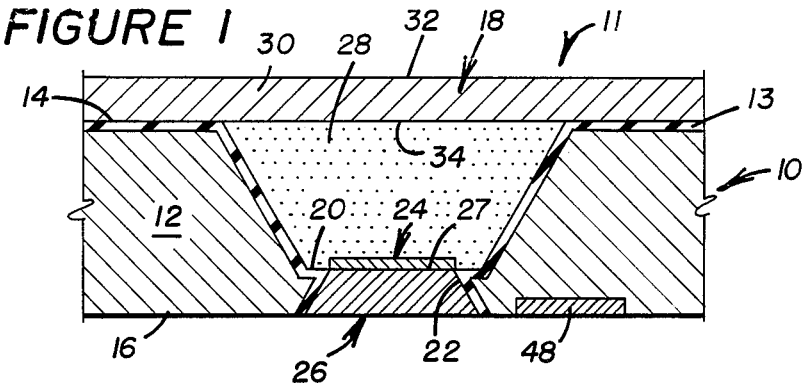
FIG. 1 illustrates, in a side sectional view, an embodiment of a microelectrochemical sensor in accordance with an embodiment of the present invention.

The present invention provides a microelectrochemical electrode structure 10 including an electrolytic cell 11, one embodiment of which is illustrated in FIG. 1. The electrode structure 10 includes a monolithic substrate 12 having a front surface 14 and a back surface 16 facing generally away from one another. The substrate 12 can be made of any of a number of materials but it is particularly advantageous to make the substrate 12 out of a semiconductor material such as silicon, silicon carbide, gallium arsenide, or the like. The invention, however, is more general in that the substrate 12 may also be made of a plastic material, a refractory oxide, or substantially any other material. It is even possible to make the substrate 12 of a conductive material, but in such an instance, and generally in instances in which the substrate 12 is made of a semiconductor material, it is necessary to provide an appropriate insulating layer 13 to prevent shorting through the substrate 12. For example, a silicon dioxide layer 13 can be formed by contacting a silicon substrate with wet oxygen at elevated temperature, e.g., about 1000° C.

It is important that the substrate 12 be monolithic i.e., a unitary structure formed of a single material, as this allows particularly easy construction and eliminates or greatly reduces problems of prior art devices. Particular problems which are eliminated or greatly reduced include (1) securing various chemistries to the electrodes especially when multilayered structures are required; (2) affixing the membranes that cover the chemistries in the wells; (3) leakage of electrolyte to the electronics; (4) the depositing of thick electrolytic mediums which are sometimes necessary; (5) encapsulation problems; (6) light sensitivity problems; (7) lack of versatility to do, for example, current as well as voltage measurements; (8) high cost; (9) incompatibilities of various chemistries with IC processing.

The electrochemical analysis which can be made in accordance with the methods of and/or using the sensors of the present invention includes voltammetric, potentiometric, coulombic, conductometric and AC analysis.

These problems exist for several reasons. First, the prior art devices build walls upwardly from a surface and the build up must be high enough to contain the chemistry. Second, encapsulation is difficult since the electronics are at the same surface as are the chemistries. Third, the gates of FET devices are exposed to light to which they are sensitive. Fourth, the electrolyte, being adjacent the electronics, can leak into the electronics. Fifth, since the electronics and chemistries are on the same surface the use of simple bump bonding techniques to connect sensors with electronics is precluded.

In accordance with the present invention a first well 18 extends into the substrate 12 from the front surface 14 and extends towards the back surface 16. All of the needed chemicals of the cell 11 are within the first well 18. The first well 18 ends in a first well bottom 20. A first passage 22 extends into the substrate 12 from the back surface 16 to the first well bottom 20. The first well 18 can be formed by any of a number of techniques, including, particularly, anisotropic etching carried out in accordance with the techniques of the semiconductor industry (in which instance the (100) face of the silicon corresponds to the front surface 14). Such a process includes such steps as cleaning the substrate 12, applying a photoresist layer, prebaking the layer, exposing the photoresist, developing the photoresist, rinsing the substrate 12, drying the substrate 12, and post baking it. Methods for carrying out each of such steps are known in the IC art and descriptions of such techniques may be found in, for example, "Integrated Circuit Engineering" by A. B. Glaser and G. E. Subak-Sharpe, Addison-Wesley Publishing Company, Reading, Mass., 1977. In this same text are found explanations of etching, oxidation of silicon, formation of a silicon nitride insulating layer, and the like.

An alternative way of forming well 18 (and passage 22 as well) is by laser drilling. Holes of various forms with lateral extensions from a few microns to hundreds of microns can be formed by this method. Depending on the depth, a process time, per hole formation, of less than 1 second can be involved. The silicon wet anisotropic etching technique has two major advantages over laser drilling. One, it is a parallel process whereby many holes can be made at once. Two, the surfaces are smooth and very well defined. The advantage of laser drilling is that it can provide straight but not smooth walled holes when such are desirable.

In accordance with an embodiment of the present invention a first electrode 24 is provided which is, very importantly, wholly between the front surface 14 and the back surface 16 and which extends at least to the first well 18. This is very important as this enables the securing of subsequent layers in a straight-forward fashion, makes the accommodation of the electrolytic medium in general easier (for example, eliminates spilling using an ink jet printer type of chemistry filling device), and allows for an easier fixing of additional barriers. Also better encapsulation is provided.

A first conductor 26 is provided in the first passage 22 and serves for electrically communicating the first electrode 24 to adjacent the back surface 16 of the substrate 12. The first conductor 26 is suitably an electronic, as opposed to an ionic, conductor. Alternatively, a well facing end 27 of the conductor 26 can play the role of the electrode 24. This feature makes the fabrication of the sensor 10 dramatically simpler. Often, however, the sensor electrode metal will need additional backup layers (e.g., aluminum or titanium) for strength and/or economy.

The first passage 22 can be made by any of the known techniques of the semiconductor art. For example, such techniques as anisotropic etching, laser drilling, aluminum thermomigration, and the like are useful. The first conductor 26 can be provided in the first passage 22, again by the techniques of the semiconductor art. For example, the first conductor 26 can be provided by such techniques as aluminum thermomigration, metal deposition, (evaporation or sputtering), electroless plating, electron beam evaporation, mechanical positioning of metal rods, melting in place with vacuum application, or the like. Aluminum thermomigration is a useful technique to make the metal contacts. This technique has the advantage of providing the hole and conductor in a single operation. In practice, however, the thermomigration technique is quite difficult and wet anisotropic etching followed by metal deposition is currently preferable.

Various types of electrode structures 10 can be formed. These include, for example, the Ag/AgCl reference electrode, platinum, platinum black, silver, gold, iridium, palladium, palladium/silver, iridum dioxide, platinum black/paladium, platinum oxide, and mixtures thereof, electronically conductive polymers, and generally any of the electrodes normally utilized in electrochemical measurements. Table 1 sets forth, as examples only, a short list of gases, and electrochemical systems which have been used to determine them.

In certain embodiments of the invention an electrolytic medium 28 is provided in the first well 18. The electrolytic medium 28 can be a liquid but more preferably is in the nature of a hydrogel, a plasticized polymeric membrane for potentiometric elements, an ion selective membrane, or a solid polymer electrolyte.

The needed materials for the various electrode structures 10 can be placed in the appropriate wells 18 as follows: pure metals if they need to be deposited from the front can be sputtered or evaporated, electron-beam or ohmic evaporation may be used, insoluble deposits of metal salts can be formed by chemical or electrochemical treatment of metals in situ. They can be deposited from the back as previously set forth. For providing the hydrogel one has the choice of lift off technology or ink-jet printer like technology. Solid polymeric electrolytes can be put in place in the same manner as hydrogels.

TABLE 1

| Gas | Electrocatalyst | Electrolyte | Potential | Sensitivity (Detection Limit*) |
|---|---|---|---|---|
| CO | Platinum-catalyzed Teflon-bonded diffusion electrode | 3.4 M $H_2SO_4$ | 1.2 V vs. NHE | 10 $\mu$A/ppm (0.2 ppm) |
| CO | Platinoid black catalyst with Teflon binder | Hydrated solid polymer (Nafion) | 1.15 V vs. NHE | 2.2 $\mu$A/ppm (0.9 ppm) |
| (CO) | Gold-catalyzed Teflon-bonded diffusion electrode | 4 M $H_2SO_4$ | (1.4 V vs. NHE) | (0.03 $\mu$A/ppm) |
| NO | Gold catalyzed | 4 M $H_2SO_4$ | >1.2 V vs. NHE | 7 $\mu$A/ppm |

TABLE 1-continued

| Gas | Electrocatalyst | Electrolyte | Potential | Sensitivity (Detection Limit*) |
|---|---|---|---|---|
| NO | Teflon-bonded Graphite with Teflon binder | Hydrated solid polymer (Nafion) | 1.25 V vs. NHE | (0.3 ppm) 2.6 μA/ppm (0.8 ppm) |
| $NO_2$ | Graphite with Teflon binder | Hydrated solid polymer (Nafion) | 0.75 V vs. NHE | −2.9 μA/ppm (0.7 ppm) |
| $NO_2$ | Gold-catalyzed Teflon-bonded diffusion electrode | 4 M $H_2SO_4$ | <1.0 V vs. NHE | −8 μA/ppm (0.25 ppm) |
| $H_2S$ | Gold-catalyzed Teflon-bonded diffusion electrode | 28% $H_2SO_4$ | 1.45 V vs. NHE | 46 μA/ppm (40 ppb) |
| $N_2H_4$ | Gold-catalyzed Teflon-bonded diffusion electrode | 23% KOH | 1.1 V vs. NHE | 40 μA/ppm (50 ppb) |
| $CH_4$ | Teflon-bonded platinum black electrode | 2 M $NaClO_4$ in γ-butyrolactane | 0.8 V vs. Ag/AgCl | 1 μA % $CH_4$ (3000 ppm) |
| $O_2$ | Gold (cathode) | Alkaline | −0.6 to −1.0 V vs. $Ag/Ag_2O$ anode** | 0.05 μA/% $O_2$ (0–100% $O_2$) |
| $O_2$ | Ultrathin electrode (gold?) | Alkaline | Lead anode** | 2.5–3 nA/ppm $O_2$ (0.1 ppm to 100% $O_2$) |
| $H_2$ | Platinum black powder | Antimonic acid | Platinum black counter electrode** | 50 μA/% $H_2$ (400 ppm) |

*Detection limit (minimum detectable quantity) is calculated as the value yielding a signal-to-noise ratio of 2, using a typical noise level 1 μA of amperometric gas sensors.
**Quasi-amperometric (polarographic), no reference.
NHE = normal hydrogen electrode.

Also, ion-selective membranes can be placed in the appropriate well(s) in the same manner as can hydrogels. Further, liquid membranes can be provided in the same manner. Composite membranes, which include enzyme based membranes, tissue cultures, living organisms, antigen-antibody and generally biocatalyst materials can also be placed in the well in the same manner.

In principle, all gases or vapors that can be electrochemically oxidized or reduced can be sensed by limiting current measurement using amperometry. The reactions occur at a characteristic potential at the electrode/electrolyte interface. An appropriate potential at which only the desired reaction proceeds must be applied to the electrode so as to obtain potential-controlled selectivity. Selectivity (or the ability to observe only one of the many possible reactions) can be either kinetic or thermodynamic in origin. Thus, the selectivity is a function of the sensing electrode catalyst and (material) potential.

An approximate indication of the suitable range of potential is provided by the reversible potentials of the reaction involved; some values are listed in Table 2. Note that each gas reaction exhibits a characteristic thermodynamic potential. An example of thermodynamic selectivity is the reduction of $NO_2$ that occurs at low potentials (Sedlak and Blurton, 1986).

TABLE 2

Thermodynamic Potentials Of Reactions Involving Gases

| Reaction | Thermodynamic Potential, E° (mV vs. NHE*) |
|---|---|
| Oxidation reactions: | |
| $HCHO + H_2O \rightarrow CO_2 + 4H^+ + 4e^-$ | −123 |
| $CO + H_2O \rightarrow CO_2 + 2H^+ + 2e^-$ | −103 |
| $H_2 \rightarrow 2H^+ + 2e^-$ | 0 |
| $C_2H_5OH + 3H_2O \rightarrow 2CO_2 + 12H^+ + 12e^-$ | 87 |
| $H_2S \rightarrow S + 2H^+ + 2e^-$ | 141 |
| $SO_2 + 2H_2O \rightarrow SO_4^{2-} + 4H^+ + 2e^-$ | 170 |
| $HCN \rightarrow \frac{1}{2}C_2N_2 + H^+ + e^=$ | 373 |
| $CH_4 + H_2O \rightarrow CH_3OH + 2H^+ + 2e^-$ | 586 |
| $NO + 2H_2O \rightarrow NO_3^- + 4H^+ + 3e^-$ | 957 |

TABLE 2-continued

Thermodynamic Potentials Of Reactions Involving Gases

| Reaction | Thermodynamic Potential, E° (mV vs. NHE*) |
|---|---|
| Reduction reactions: | |
| $O_3 + 2H^+ + 2e^- \rightarrow O_2 + H_2O$ | 2076 |
| $Cl_2 + 2e^- \rightarrow 2Cl^-$ | 1360 |
| $O_2 + 4H^+ + 4e^- \rightarrow 2H_2O$ | 1230 |
| $NO_2 + H^+ + e^- \rightarrow HNO_2$ | 1093 |
| $CO_2 + 2H^+ + 2e^- \rightarrow HCOOH$ | −199 |

*NHE = normal hydrogen electrode

Because $NO_2$ is reduced to NO and the NO product is not further reduced, the $NO_2$ sensor (with sensing electrode operated at low potentials) is selective for $NO_2$, having no signal for the NO that may be present. This $NO_2$ selectivity results from control of the sensing electrode's potential in a range such that no NO reactivity is observed. The potential of the electrochemical cell has been compared to the temperature of a catalyst surface (Blurton and Stetter, 1977), which also may be used for control of the catalyst reactivity. Control of the potential is accomplished in many sensors by using three electrodes and a potentiostatic circuit.

More exact information as to a suitable range of potentials is afforded by the kinetics of the oxidation or reduction reaction, which can be discussed only in terms of electrocatalysis. Each electrocatalyst formulation will have unique properties. The activity of platinum for CO oxidation has been found to be $10^3$ to $10^6$ times better than that of gold. This is a good example of kinetic selectivity. Both reactions occur on both metals, but one is orders of magnitude more rapid than the other. Although the presently available sensors utilize expensive, noble metal catalysts, the required amount of such a catalyst for each sensing element in electrode structures 10 in accordance with the present invention is minimal because the sensor is a microsize device. Moreover, inexpensive electrocatalysts based on polymer materials that exhibit catalytic activity and selectivity as high as those of noble metals can be used in place of the noble metals.

If the gas to be sensed exists in a mixture containing several reactive components that exhibit close thermodynamic selectivity potential (cf. Table 2), the concentration of the desired component can be determined selectivity by the differential pulse voltammetry (DPV) technique. Let us consider a simple example where a mixture of Gas A and Gas B exists. Gas A and Gas B would exhibit current vs. potential curves with different limiting currents $I_A$ and $I_B$. By differentiating these curves, one obtains two sharp clearly separated peaks with different characteristic potentials, $E_A$ and $E_B$. The peak current values are proportional to the gas concentrations. Thus, the DPV technique, in addition to an improved signal-to-noise ratio, can provide potential-controlled selectivity to an electrochemical sensor through precise measurements of $E_{peak}$ values, which are closely related to the thermodynamic potentials given in Table 2 and are characteristic to each gas species.

Among useful electrolytes, particularly for amperometric elements are solid electrolytes, including solid polymeric electrolytes such as Nafion (a trademark of DuPont) which is part of a class of solid polymeric ion exchangers which conduct ions upon exposure to water. Probably the best known examples are membranes made from polystyrene with fixed negative sites (sulfonate, carboxylate or phosphonate) or fixed positive sites (quaternary ammonium or quaternary phosphonium). Selection as far as ions are concerned with these materials is almost exclusively on the basis of charge and for ions with the same charge discrimination is very slight. For amperometric sensing the use of these materials is relatively new. Other examples of solid polymeric electrolytes besides Nafion (which is a perfluorinated ionomer) are sulfonated styrene-divinyl benzene resins and divinyl napthalene sulfonic acid polymer.

Such polymers are characterized chemically and physically in that they have a hydrophobic nature with ionic (hydrophilic) clusters inside. They conduct ions upon hydration. They exclude co-ions up to the Donnan failure point at which stage ions of both types can penetrate into the resin. Neutral molecules can diffuse readily through such membranes and especially large organic molecules can dissolve within the more hydrophobic resins.

Resins can also be used as reference solutions (see, for example, French patent publication No. 2,158,905). These ion exchange resins have been used as the electrolytic medium for a potentiometric $CO_2$ sensor (see, for example, U.S. Pat. No. 3,730,868).

For potentiometric elements membranes can comprise a polymeric binder or support impregnated with a solution of an ion selective carrier or ionophore in a solvent for the ionophore. Membranes of this type can be tailored to sense particular ions selectively. For example, for sodium the antibiotic nonactin can be used as the ionophore in a PVC matrix plasticized with dioctyl sebacate. For potassium, valinomycine would replace the nonactin.

Useful gels for incorporation within the sensor structure include, without limitation: methylcellulose, polyvinyl alcohol, agar, carboxycellulose, gelatin, agarose, deionized gelatin, polyacrylamide, polyvinyl pyrrolidone, hydroxyethylacrylate, hydroxyethylmethacrylate, and polyacrylic acid. They are characterized in that they constitute thickened (more viscous) solutions. They are hydrophilic in natural and include synthetic polymeric film forming materials.

In certain cases the electrolytic medium 28 can come from a solution being analyzed. In most cases where the electrolytic medium 28 is present, however, it is provided during the construction of the electrode structure 10. Often it will be undesirable to allow a solution being analyzed to mix with and/or directly contact the electrolytic medium 28.

A barrier 30, generally in the nature of a membrane, can cover the first well 18. The barrier 30 has an outfacing surface 32 and an infacing surface 34 and the infacing surface 34 is in flow contact with the electrolytic medium 28 so as to provide a full conductive path. Indeed, the barrier 30 can be at least partially within the first well 18. The barrier 30 provides entry into the electrolytic medium 28 of a selected moiety in response to contact of a selected species with the outfacing surface 32 of the barrier 30. Either the selected species will pass through the barrier 30 and will then constitute the selected moiety, or contact of the selected species with the barrier 30 will lead to the introduction of a different moiety into the electrolytic medium 28. The barrier 30 is generally at least substantially impermeable to the electrolytic medium 28 to prevent escape and/or mixing with the analyte solution exterior of the barrier 30. The barrier 30 would not be present, or would be permeable to a solution being analyzed, in those instances when the solution constitutes the electrolytic medium 28.

The barrier 30 may encapsulate the entire electrode structure 10 including the front surface 14 and the back surface 16. Alternatively, the barrier 30 may only cover the first well 18, or the first well 18 and part or all of the front surface 14. It may be desirable to encapsulate the remainder of the electrode structure 10, or even all of the electrode structure 10 including the barrier 30, as a protection against contamination. Generally, an inert encapsulating layer (not shown) will serve the purpose. The encapsulating layer, when present, must provide access (via, for example, pores or holes therethrough) to the first well 18 or to the barrier 30 covering the first well 18. It can be formulated as can the barrier 30.

A number of materials may serve as the barrier 30. For example, the barrier 30 can comprise a gas pervious liquid impervious membrane. This is useful in the situation wherein the sensor is used in a liquid to detect dissolved gases, for example, if the electrode structure 10 is utilized in blood.

Other types of materials for utilizing as the barrier 30 are TEFLON membranes, silicone rubber membranes, silicon polycarbonate rubber membranes, mylar, nylon 6, polyvinyl alcohol, polyvinyl chloride, methylcellulose, cellulose acetate, high density polyethylene, polystyrene, natural rubber, fluorosilicone, dimethylsilicon rubber, any appropriately perforate photoresist polymer, and dimethylsilicon. It is generally preferred that the membranes utilized be solution castable so as to make fabrication of the membrane more easily accomplished.

The barrier 30 can be placed over appropriate of the wells 18 by, for example: solution casting, separate casting on a different substrate and physical transfer, heat shrinking in place, solution casting utilizing an ink-jet printer, spin coating, or dip coating. If the barrier is in the nature of uniform latex microspheres, made for example of polystyrene, styrene-butydiene, or TEFLON, such microspheres can be placed in position utilizing the ink-jet technique, by dipping, by solvent spraying, or the like. If the barrier is of the nature of or includes activated carbon or similar materials it can be placed in position by ink-jet printing, solvent casting, or the like. If the barrier includes, for example, permanganate coated alumina or other substance which serves to remove nitric oxide, it can be placed in position similarly to the carbon particles.

The microelectrochemical electrode structure 10 just described may serve as a working or sensing electrode, a reference electrode, or a counter or auxiliary electrode. As may be seen in FIG. 2 a single substrate 12 may have one or more each of a sensing electrode cell 29, a reference electrode cell 31, and a counter electrode cell 33 thereon with appropriate provision, e.g., salt bridges 35,37, being made for ionic conductivity between the various electrode cells, or more particularly between the various electrolytic mediums 28,39,41 contacting the various electrodes. The salt bridges 35,37 are necessary when barrier 30 is a barrier for all ions.

Note that the designations S, R and C are used in the figures to indicate, respectively, sensing, reference and counter electrodes.

Figure 2:
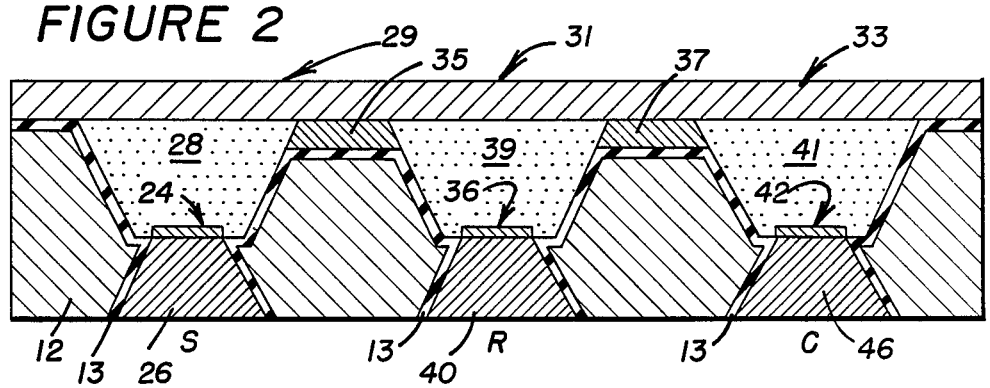
FIG. 2 illustrates, in similar view, an alternate embodiment of the present invention.

If the first electrode 24 is a sensing electrode the substrate 12 will also include a reference electrode 36 in ionic electrical communication with the first electrode 24. The reference electrode 36 will also be electrically isolated from the sensing electrode 24 other than via the electrolytic medium 28. For example, if the substrate is silicon an appropriate silicon dioxide or silicon nitride layer 13 can be conventionally deposited or formed in the first well 18 and in the first passage 22. The reference electrode 36 can also be provided with its own different electrolytic medium 39 (FIG. 2) containing the species which determine the reference electrode potential. Also, the counter electrode 42 can be provided with a separate electrolytic medium 41 (FIG. 2).

Figure 3:
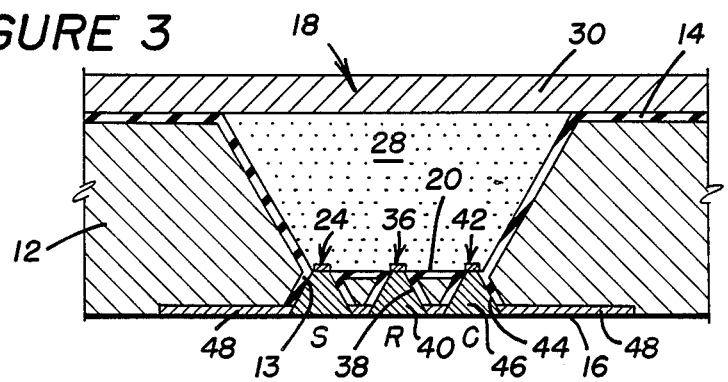
FIG. 3 illustrates, in similar view, an alternate embodiment of the present invention.
Figure 4:
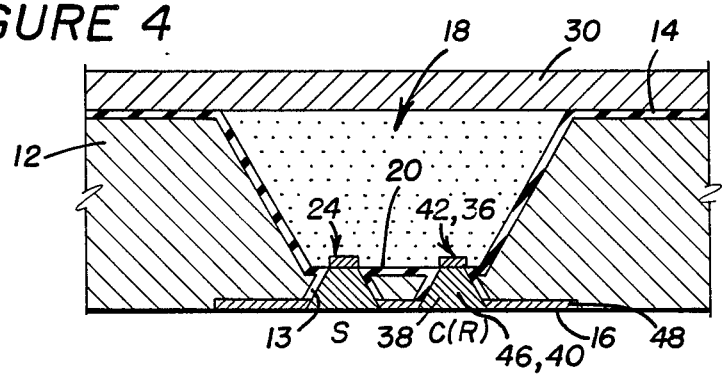
FIG. 4 illustrates, in similar view, an alternate embodiment of the present invention.

In the embodiment illustrated in FIGS. 3 and 4 the sensing electrode 24 and the reference electrode 36 are each in the first well 18. In such an instance the substrate 12 has a second passage 38 extending from the back surface 16 of the substrate 12 to the reference electrode 36 in the first or sensor well bottom 20. A second conductor 40 is in the second passage 38 and serves for electrically communicating the reference electrode 36 to adjacent the back surface 16 of the substrate 12. If the substrate is silicon the silicon dioxide or silicon nitride layer 13 also extends along the second passage 38.

A counter electrode 42 is provided in those instances when such is necessary, for example, for making nonpotiometric measurements. The counter electrode 42 (see FIG. 3) is in ionic electrical communication with the electrolytic medium 28 and is electrically isolated from the sensing electrode 24, and from the reference electrode 36 (when such is present), other than via the electrolytic medium 28. The counter electrode 42 may be in the same well 18 as is the sensing electrode 24, as illustrated, for example, in the embodiments of FIGS. 3 and 4. And, the counter electrode 42 can, be in the same well as is the reference electrode 36 as in the embodiment of FIG. 3. The counter electrode 42 may be in the same well 18 as is the sensing electrode 24, that is it may be in the first well 18. This embodiment is seen in FIGS. 3, 4, 11, 12 and 13.

In the structure of FIG. 3 the substrate 12 has a third passage 44 extending from the back surface 16 thereof to the first well bottom 20. A third conductor 46 is located in the third passage 44 and electronically communicates the counter electrode 42 to adjacent the back surface 16 of the substrate 12.

In the case of FIG. 4 the counter electrode 42 also plays the role of reference electrode 40. The silicon dioxide or silicon nitride layer 13 provides needed insulation.

Figure 5:
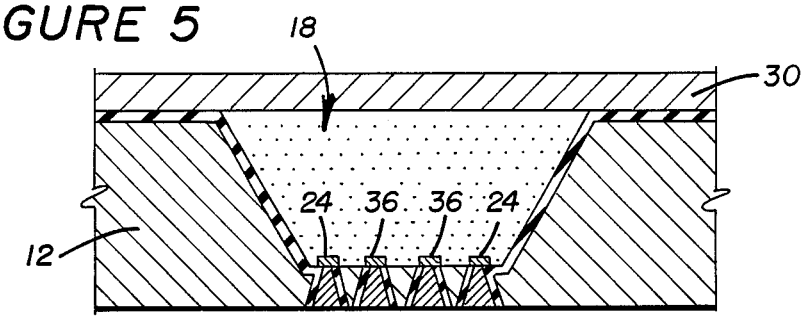
FIG. 5 illustrates, in similar view; an alternate embodiment of the present invention.

In certain instances, for example, AC measurements, conductometric measurements, and the like, it may be desirable to have more than three electrodes in a single well 18. FIG. 5 illustrates such a structure.

In a particular instance (not shown) the well 18 can be in the nature of a trench in which electrophoresis is carried out by providing a potential gradient along the length of the trench. Appropriate sensing electrodes 24 are spaced along the bottom of the trench whereby various species can be determined. Appropriate reference 36 and/or counter electrodes 42 are also provided along the bottom of the trench.

Electronic circuitry 48 can advantageously be included in certain embodiments of the present invention in the substrate 12 adjacent the back surface 16 thereof. Such electronic circuitry 48 is adapted for, and serves for, processing signals from one or more of the sensing electrode 24, the reference electrode 36, and the counter electrode 42. The electronic circuitry 48 can be formulated by conventional integrated circuit fabrication techniques. Generally the circuitry will serve to convert the signals from high impedance to low impedance and may also amplify the signals from the electrodes, and, if desired, perform computational tasks and present the data in condition for display or printing out, for example as concentrations of the species being detected. The length(s) of the conductor(s) 26,40 and/or 46 in such instances can be kept extremely short leading to a very high signal-to-noise ratio and, therefore, increased sensitivity. Note also that the chemistry in the first well 18 is completely isolated from the electronic circuitry 48 whereby the integrity of the latter is protected.

As an alternative to having the electronic circuitry 48 on the back surface of the substrate 12, the electronic circuitry 48 can instead be on a separate semiconductor substrate 50 (see FIG. 6) which abuts the back surface 16 of the substrate 12. This provides encapsulation and protection of the electronic circuitry 48.

Figure 6:
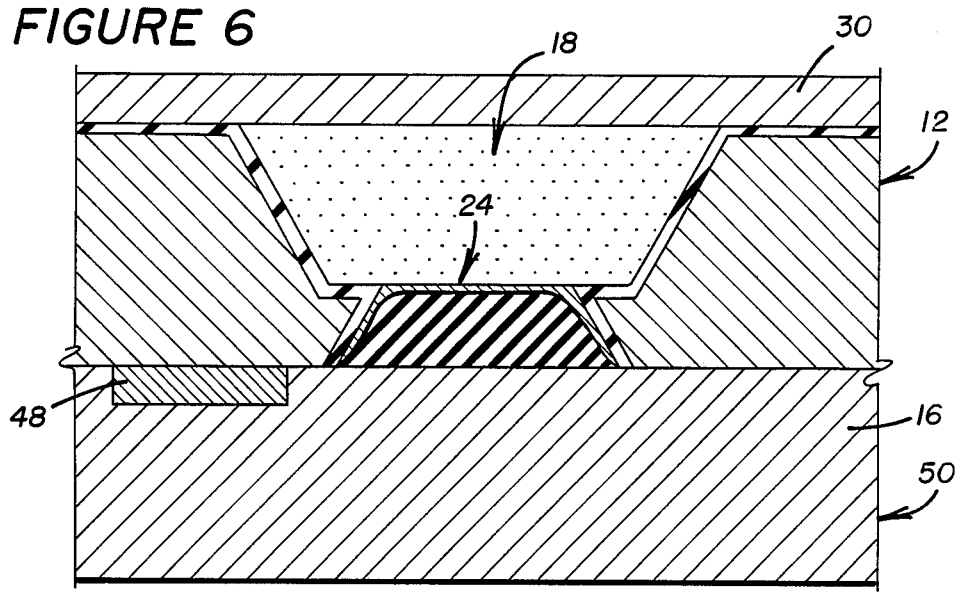
FIG. 6 illustrates, in similar view, an alternate embodiment of the present invention.
Figure 7:
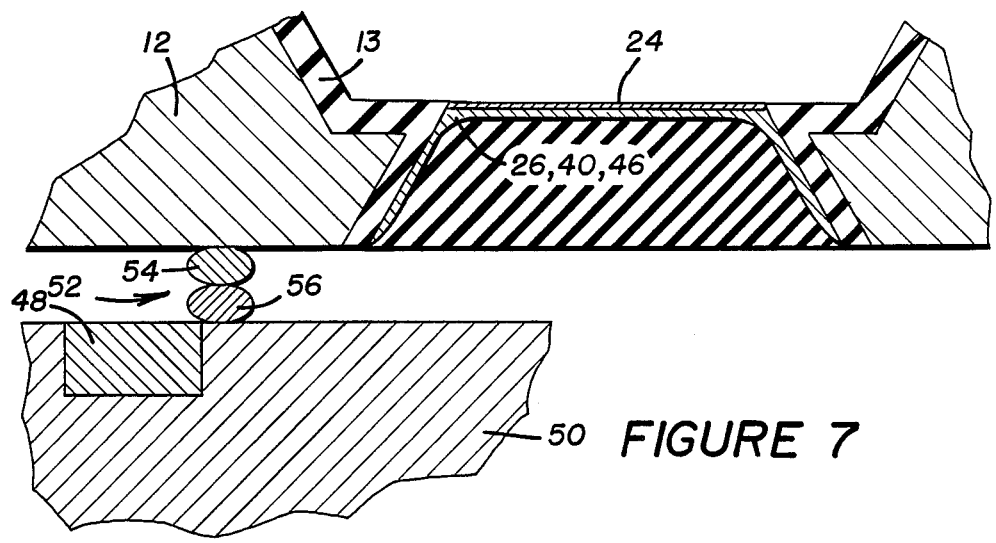
FIG. 7 illustrates a detail in the embodiment of FIG. 6.

FIG. 7 is an enlarged view of a portion of FIG. 6. It illustrates the use of a bump bonding techniques to make the needed electrical connection between the conductor (26, 40 and/or 46) and the electronic circuitry 48. The bump bonding site 52 is spaced from the electrode (24,36 and/or 42) whereby the contents of the cells (29,31,33) are not damaged by heat during bump bonding. Also, this allows good bump bonding contact to be made whereby the resulting bond has good mechanical strength. Basically, the bump bonding is carried out by pressing the bumps 54,56 together and heating the substrate 50. The bumps 54,56 can be of very different thickness. Good results have been obtained with the bump 54 of silver and about 2000 Angstroms thick and with bump 56 of copper and about 10 microns thick.

FIG. 7 also illustrates the technique of providing the first electrode 24 by depositing a small amount of an electrode material, e.g., platinum, silver, etc., followed by depositing the first conductor 26,40,46. In such an instance the first electrode 24 forms a portion of the bottom 20 of the first well 18. Also illustrated is filling in the passage 22,38 or 44 with a support material, e.g., a polymer such as a polyimide.

Figure 8:
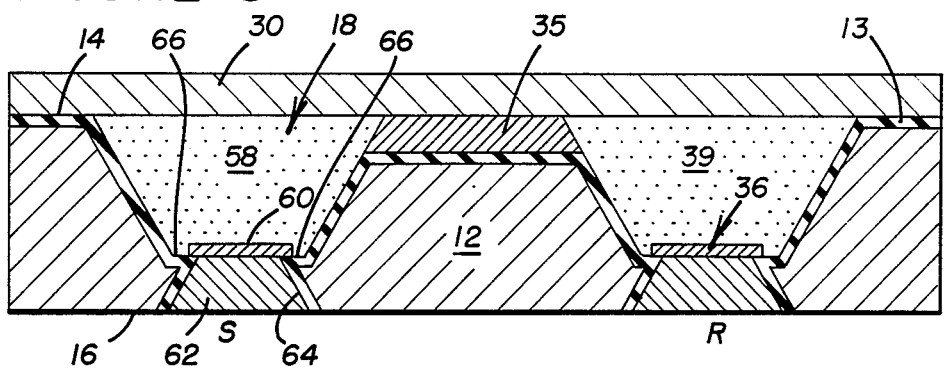
FIG. 8 illustrates, in similar view, an alternate embodiment of the present invention.

In accordance with one embodiment of the present invention, for example, as illustrated in FIG. 8, the reference electrode 36 is of the nature described above. The working or sensing electrode structure 24, on the other hand, is in the nature of an ion-selective membrane 58 (as described previously) covering a sensing electrode base 60 which is attached to a sensing conductor 62 in a passage 64 which leads from a bottom 66 of the sensing electrode well 18 to the back surface 16 of the substrate 12. The analyte medium makes the electrolytic contact between the ion-selective membrane 58 and the reference electrode 36. In this instance the barrier 30 is ion transparent or can be omitted. Note that the electrolytic medium 39 is not the same material as is the ion-selective membrane 58.

Any of a number of ion selective membranes 58 can be used. For example, such membranes are disclosed by M. A. Arnold and R. L. Solsky Anal. Chem. 1986, 58, 84R–101R, M. E. Meyerhoff and Y. M. Fratecelli, Anal. Chem. 1982, 54, 27R–44R, M. A. Arnold and M. E. Meyerhoff, Anal. Chem. 1984, 20R–48R, and J. Koryta, Analytica Chimica Acta, 159, ·84, 1–46.

Figure 9:
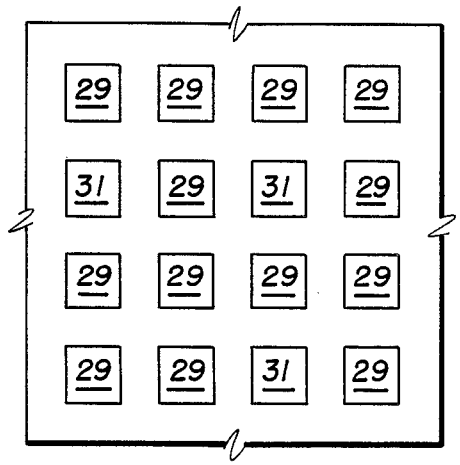
FIG. 9 illustrates, in plan view, an array of microelectrochemical sensors in accordance with an embodiment of the present invention.

It is anticipated that in accordance with the present invention an array of sensing cells can be provided with occasional reference cells 36. One such array is illustrated in FIG. 9. In the particular configuration shown in FIG. 9 each reference cell 31 is surrounded by, and can serve as the reference cell 31 for, several different sensing cells 29.

It is also contemplated in accordance with the present invention that on any substrate 12 more than one sensing cell 29 can be utilized for each chemical species being analyzed. That is, there can be two or five, or ten, or any desired number of sensing cells 29 which detect, for example, carbon monoxide. This provides extra selectivity by means of chemometrics, redundancy, and reliability in case any of the carbon monoxide sensing cells 29 fail whereby the electrode structure 10 would continue to operate Chemometrics is the technique of mathematically treating data from a plurality of sensors to improve the selectivity of the analytical results (see, for example, Stetter, J. R., Jurs, P. C., and Rose, S. L., Anal. Chem. Vol. 58, pp 860–866 (1986)).

Figure 10:
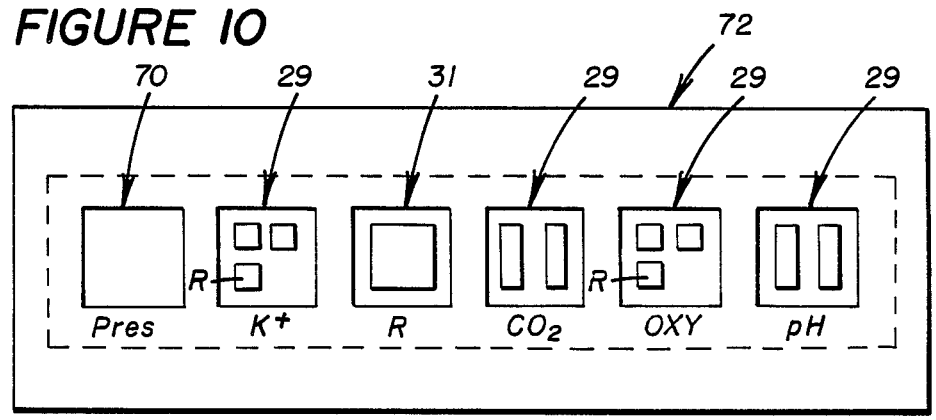
FIG. 10 illustrates, in plan view, an alternate array of microelectrochemical sensors in accordance with an embodiment of the present invention.

FIG. 10 illustrates an embodiment of the invention wherein a plurality of sensing cells 29 are provided, some of which can be for different constituents than others, e.g., oxygen, carbon dioxide and $K^+$. One or more, in FIG. 10 a single reference cell 31, is also present as is a pressure sensor 70. The various cells 29,31 and the pressure sensor 70 are arranged linearly whereby the total lateral extension (width) of the array 72 of electrode structures 10 can be restricted to be no more than about 300 microns. The length of the array of the various cells 29,31 and the pressure sensor 70 is determined by the number of such cells (plus the pressure sensor 70) can be restricted to be no more than about 150 microns multiplied by the number of cells plus the number of pressure sensors 70. The pressure sensor 70 can be a conventional piezoresistive-type pressure sensor of the nature described in, for example, Borky, J. M., IEEE Trans. On. Elect. Dev. Vol. ED-26, No. 12, December 1979.

The use of a multiple array of microelectronic chemical sensors allows the quantitative detection of different gases and organic vapors to further increase selectivity, to include redundancy, to increase reliability, and to permit use of chemometrix. Also, it is possible to include different types of sensors within such an array. For example, the internal temperature of a sensor can be monitored to compensate for known parameter changes with temperature. Also, a microhumidity sensor can be incorporated.

Each microelectronic chemical sensor can comprise a different electrocatalyst coating so that each sensor is as specific as possible to a certain gas or vapor. As a result, such a sensor comprising an array of optimized microsensors exhibits a maximum selectivity to a given mixture of gases and/or vapors. The presence of extra sensor elements with the same configuration and catalysts allows not only for averaging the signals of identical elements but also for correcting signals of dissimilar elements.

All existing electrocatalytic coatings are imperfectly selective, but the extent to which they fail to be selective is different for each. If one uses an array of several microsensor devices instead of a single one and coats each with a different electrocatalyst film, the relative responses of all the microdetectors to a given gas or vapor concentration is different. The pattern of these responses is specific of a given gas or vapor (provided each microsensor exhibits reproducible signals), even if the electrocatalysts coatings are not individually sensitive to a single gas or vapor. Therefore, the sensor array can yield more information than single sensors and can be used to identify and quantify many gases and organic vapors.

Unraveling vapor spectral data from an array of microsensors in a gas or vapor detection system is possible with a microcomputer that uses innovative signal-processing techniques to overcome inherent limitations of the single sensor elements. Pattern-recognition methods can be used to determine the uniqueness of the information obtained and the capacity of each of the channels for classification. Recently, such a pattern recognition analysis of data from an electrochemical sensor array has been successfully applied for the detection of hazardous gases and vapors (Stetter, Jurs and Rose, 1986).

For the simplest case, the array containing n individual sensors that are operated amperometrically, yields n channels of data for an unknown chemical species detected. The n-channels sensor responses for each compound are normalized so that the strongest channel equals 1 (or $-1$, if a negative number). This normalized set of response is termed a pattern vector as follows:

$$X_i = (x_i, x_2, \ldots x_j, \ldots x_n), \quad (4)$$

where $X_i$ is the pattern vector for compound 1, and $x_j$ are the sensor responses from 1 to n. The pattern vector is concentration-independent and can be compared to a library of pattern vectors of known compounds. That with the closest match is the identified compound. The concentration can be calculated using the strongest channel of the identified pattern vector. Thus, arrays of electrode structures 10 have the capability of identifying an unknown gas or vapor from a known set of gases and vapors.

FIG. 11 illustrates a portion of the embodiment of the linear array of FIG. 10 and shows the structure of the pressure sensor 70. At the bottom of the well 18 is a flexing membrane 71 which can flex into a cavity 73 between a support 75, which may be made of any convenient material, e.g., glass, plastic or a semiconductor such as silicon. Element 70 is the pressure sensing element. Piezoresistors can be diffused in the back of the thin silicon membrane and all electronics are protected with, for example, a Mallory bonded glass piece (the support 75). The cavity 73 in the support 75 provides space for the electronics and can be evacuated to make an absolute pressure sensor possible.

FIG. 12 shows an embodiment of the invention wherein each of the sensing electrode 24 and the counter electrode 42 are in the first well 18. The reference electrode 36 communicates with the first well 18 via a pinhole 76 whereby the chemistry of the reference electrode cell 31 is kept separate from but communicates electrically with the electrolytic medium 28 in the first well 18. The reference electrode 36 is adjacent the back side 16 of the substrate 12 and is closed off by an enclosure 78 which may be merely an extension of the reference electrode 36, or which can alternatively be of a different material. The original filling of the reference cell 31 is from the back side 16 of the substrate 12.

FIG. 13 shows an embodiment of the invention wherein the sensing and counter electrodes 24,42 are in a single well 79, while the reference electrode 36 is in a separate well 81. An appropriate salt bridge 83, or its equivalent, provides ionic conductance between the electrolytic mediums 28 and 39. This is a typical structure for conductometric and voltammetric measurements, for example, a Clark oxygen sensor.

Figure 14:
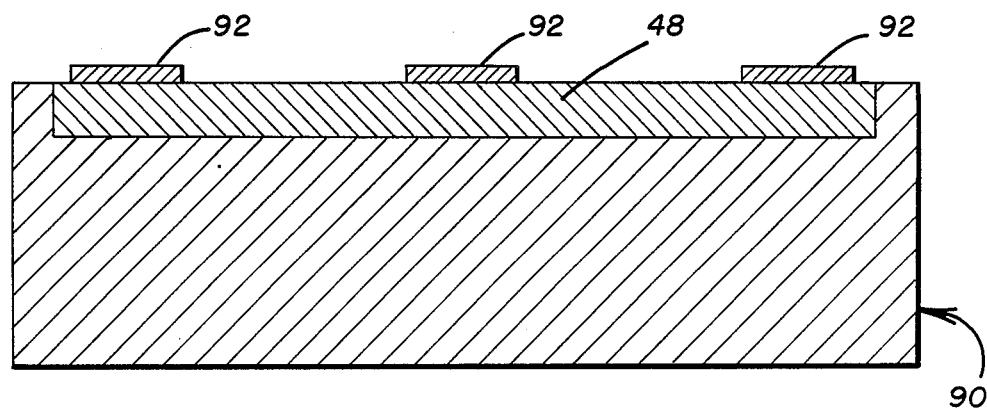
FIG. 14 illustrates, in a side sectional view, a separate electronics containing member useful in an alternate embodiment of the present invention.

In certain instances it may be desirable to have the electronic circuitry 48 on a separate member 90 (see FIG. 14) which, via appropriate contacts 92 can form temporary electrical contact with the appropriate conductors 26,40 and/or 46 (for example, as seen in FIG. 2) during determination of the concentration or presence of one or more species. In this manner, a single member 90 can provide the needed electronic circuitry 48 for a plurality of electrode structures 10. Also, if the electrode structure 10 is used in an environment where it must be more or less permanently installed and where it has only a short useful lifetime, only the electrode structure 10 need be replaced and not the electronic circuitry 48 (since the latter need only be exposed to the environment during the actual time of measurement).

The first well 18 can be made any convenient depth. It is preferred that the first well 18 extends sufficiently towards the back surface 16 of the substrate 12 whereby the first electrode 24 is sufficiently deeply positioned within the first well 18 whereby electrochemical reaction of the selected moiety at the first electrode 24 provides a substantially Nernstian slope. In general, this means that the first well 18 should be sufficiently deep so that the electrolytic medium 28 (when present), or the membrane portion of the ion-selective electrode (when present), while remaining entirely within the first well 18, extends above the first electrode 24 a distance of at least about 40 microns.

Generally it is preferred for cells including an ion-selective membrane that the first well 18 extends towards the back surface 16 of the substrate 12 from about 40 to about 200 microns. When there is more than one electrode in the first well 18 the back surface 16 of the substrate should be close enough to the bottom of the well so that shunting does not occur between respective conductors. For example, the back surface 16 can be from about 10 to about 100 microns from the first well bottom 20. This assures very short contacts and also allows inexpensive anisotropic etching techniques (which provide tapered passages, as illustrated) to be used to form the first passage 22, and, if necessary, the second passage 38 and/or the third passage 44. As the etching is anisotropic in such an instance the widths of the passages 22, 38 and 44 at the back surface 16 could otherwise become so wide that the conductors 26, 40 and/or 46 met before or at the back surface 16.

If laser drilling is used to form the passages 22,38 and/or 44 this problem does not exist but laser drilling will not produce as many cells per unit time since the laser must be repositioned to drill each passage. However, particularly when anisotropic etching is utilized, it is preferred that the sensor well 18 extends from about 60 to about 125 microns towards the back surface 16 and it is preferred that the back surface 16 is from about 10 to about 40 microns from the sensor well bottom 20. A particularly preferred structure is one wherein the sensor well 18 is approximately 100 microns deep and the back surface 16 is about 25 microns from the sensor well bottom 20. The same preferences hold with respect to the size of the reference well and the counter well, if such is present.

For voltammetric elements and $CO_2$ a thinner electrolytic medium 28 over the sensing electrode 24 can be more appropriate, for example, between 20 and 50 microns. Thus, the first well 18 and other wells as well can be only partially filled with the appropriate electrolytic medium 28,39,41.

The invention will be better understood by reference to the following examples which show the construction and testing of certain substructures in accordance with the present invention.

EXAMPLE 1

Macroelectrochemistry

The pH response of an $IrO_2$ electrode was tested in physiological saline solution in the pH range 6.0–8.0. The measuring cell consisted of a 1 $\mu$m thick $IrO_2$ electrode separated from a Ag/Cl electrode by 50 $\mu$m. The electrodes were fabricated on the surface of a silicon substrate coated with silicon dioxide. Adhesion layers were used of 100 Angstroms Ti for $IrO_2$ and 50 Angstroms each of Ti and Pd for Ag. AgCl was formed by bringing Ag in contact with a 1% $FeCl_3$ solution for two minutes. The potential of the Ag/AgCl electrode was first checked against a saturated calomel electrode and it agreed with the literature value. The response of the $IrO_2$ electrode was then measured using this Ag/AgCl electrode reference.

Two electrodes gave near Nernstian responses, but third and fourth electrodes gave super- and sub-Nernstian responses, respectively. It is believed that non-optimized sputtering conditions led to the non-Nernstian electrodes and that close to 100% yield of well-behaving (Nernstian) electrodes are producible by optimizing the sputtering conditions.

EXAMPLE 2

The $IrO_2$ electrodes of Example 1 which gave near-Nerstian response were used in the fabrication of $CO_2$ electrodes. A 5% solution of poly(hydroxy ethyl methacrylate) in 95% ethanol was painted onto the $IrO_2$-AgAgCl electrode area. The solvent was allowed to evaporate. The dried polymer was equilibrated with $10^{-3}$M $NaHCO_3$+0.1M NaCl. The gel and the electrolyte were then allowed to dry up. 4.75% polysiloxane-polycarbonate solution was painted on top of the gel. Again, the solvent was allowed to dry completely. The completed electrode was checked for its response to $CO_2$. Different concentrations of $CO_2$ were generated by adding known volumes of 0.1M $NaHCO_3$ solution to 0.1M HCl. It was assumed that all $NaHCO_3$ was converted to $CO_2$. The change in potential of the electrodes was as follows:

| Concentration of $CO_2$ | Potential v. SCE |
|---|---|
| 10E-5–10E-4M | 38 mV |
| 10E-4–10E-3M | 61 mV |
| 10E-3–10E-2M | 59 mV |

These changes were reproducible to ×2 mV. The response time of the electrode was approximately 60 seconds. The response time and detection limit can be improved by controlling the thickness of the polymer membrane and the composition and thickness of the hydrogel. No attempt was done to optimize them in the planar structure.

EXAMPLE 3

Work with planar $O_2$ sensors has determined that silver with an adhesion layer of titanium and palladium provides superior adhesion to $SiO_2$ substrates than does platinum, and at the same time gives a current plateau similar to that of platinum. It has also been established that a two electrode system is as satisfactory as a three electrode system in giving a wide current plateau. The counter electrode in a two electrode system can be either bare Ag or Ag/AgCl. However, it was observed that a longer current plateau results using chloridized Ag. Also, the drift was considerably less in this case.

The response of the electrode was checked in phosphate and carbonate buffers. Although there was a decrease of current on shifting from phosphate to carbonate buffer a longer plateau was obtained. It has been observed by other workers that use of carbonate buffer will reduce interference from $CO_2$.

Poly(HEMA) was chosen as the first hydrogel for testing since it has been found satisfactory by other workers. However, a new current peak at around −0.1 V was observed in the voltammogram for the electrode in the presence of poly(HEMA). It is believed that this peak is due to some impurities (residual cross-linking agent, redox initiator, etc.) which could be present in the hydrogel. In this case, purification of the hydrogel will be necessary.

After assembling all the components, the sensor was completed by casting a silicone/polycarbonate membrane over the whole structure. It was observed that the electrode decreased after this step.

EXAMPLE 4

A practical example of the current invention is a sensor for pH, $CO_2$ and $O_2$ in blood.

Three electrolytic cells 11 are made in a top silicon part fitting in a 20 gauge catheter. A matching bottom silicon part contains the necessary electronics. The bottom part has 10 microns high copper bumps that have been found to make a satisfactory bump bond to silver which is on the back surface 16 of the substrate 12. The sensing well 29 which is intended for pH sensing has besides the general outlook of FIG. 4 the following specifics. One electrode in the pH sensing well 29 consists of iridium dioxide and one electrode consists of Ag/AgCl. The $IrO_2$ electrode is made by reactive sputtering through a silicon mask from the back of substrate 12. A promotion layer titanium is also sputtered on, as well as an iridium layer to make a better performing iridium/iridum dioxide electrode. Finally Ag is used to back up these layers. The order of the depositions just mentioned is as follows:

1. Titanium—50 to 100 Angstroms promotion layer
2. Iridium dioxide—2000 to 5000 Angstroms
3. Iridium—2000 to 5000 Angstroms
4. Silver—2000 Angstroms Again the silver is there as a back-up layer and contact material to the bumps 54,56 (FIG. 7) and comes on last. In order to expose iridium dioxide to the electrolytic medium a short titanium etch is needed to free the iridium dioxide. The titanium remaining on the silicon dioxide walls after the etch helps the adhesion of iridium dioxide to the sidewalls of the passage 22. The iridium-/iridium dioxide electrode was shown to give a very match with theoretical predicted potentials on a microscale. The Ag/AgCl electrode was made with the following steps:

1. Titanium—50 to 100 Angstroms of adhesion promotion
2. Palladium—50 to 100 Angstroms of adhesion promotion plus corrosion prevention
3. Silver—2000 to 3000 Angstroms As in the case of iridium dioxide a short etch is used to expose the silver to the electrolytic medium. The Ag-/AgCl was shown to behave as a microscopic Ag-/AgCl reference electrode. The chlorinization was accomplished with a 1% $FeCl_3$ solution.

The oxygen electrolytic sensing cell 29 is made in one of two fashions:

A.
1. Silver cathode
2. Ag/AgCl reference electrode the materials fabrication is the same as mentioned above:

B.
1. Platinum cathode
2. Ag/AgCl reference electrode
3. Platinum counter-electrode In case "A" the cathode area should be about one-fifth to one-tenth of the anode area. The best buffer solution identified for the electrolytic medium in the case of the oxygen sensor 29 is a carbonate buffer.

The material of the barrier 30 identified as a good choice for the $CO_2$ and $O_2$ element is a block copolymer of polycarbonate with silicone rubber. This product (e.g., General Electric MEM-213) can be heat sealed and is heat shrinkable. It can be easily solution cast. The solvents used to cast this membrane are, for example, toluene or dichloromethane.

To open up the membrane where it is not needed (i.e., the small pH cell in this case) the membrane can be locally laser cut or it can be locally dissolved. The $CO_2$ cell 29 contains the same electrodes as the pH cell 29 except that in this case we do have an electrolytic medium, a buffer, covered by the same membrane as ;mentioned with respect to the oxygen cell.

Industrial Applicability

The present invention provides a microelectrochemical electrode structure 10, and arrays thereof on a substrate 12. Such electrode structure 10 and arrays of electrode structures 10 on a single substrate 12 are useable for detecting low concentrations of gaseous, ionic and nonionic species.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A microelectrochemical electrode structure, comprising:
   a monolithic substrate having a front surface and a back surface facing generally away from one another, a first well extending into said substrate from said front surface towards said back surface and ending in a first well bottom, and a first passage extending into said substrate from said back surface to said first well bottom;
   a first electrode wholly between said front and back surfaces of said substrate; and
   a first conductor in said first passage electrically communicating said first electrode to adjacent said back surface.

2. An electrode structure as set forth in claim 1, further including:
   an electrolytic medium in said first well;
   a barrier having an outfacing surface and an infacing surface covering said first well with said infacing surface in flow contact with said electrolytic medium, said barrier providing entry into said electrolytic medium of a selected moiety in response to contact of a selected species with said outfacing surface and being at least substantially impermeable to said electrolytic medium.

3. An electrode structure as set forth in claim 2, wherein said first well extends sufficiently towards said back surface and said first electrode is sufficiently deeply positioned in said first well whereby electrochemical reaction of said moiety at said first electrode provides a substantially Nernstian slope.

4. An electrode structure as set forth in claim 3, wherein:
   said substrate has a reference well extending into said substrate from said first surface towards said back surface and ending in a reference well bottom and a reference passage extending from said back surface to said reference well bottom; and
   a reference electrode in said reference well;
   and further including:
   a reference conductor in said reference passage electrically communicating said reference electrode to adjacent said back surface.

5. An electrode structure as set forth in claim 4, wherein:
   said substrate has a counter well extending into said substrate from said surface towards said back surface and ending in a counter well bottom and a counter passage extending from said back surface to said counter well bottom; and
   said counter electrode is in said counter well;
   and further including:
   a counter conductor in said counter passage electrically communicating said counter electrode to adjacent said back surface.

6. An electrode structure as set forth in claim 9, wherein said barrier further covers said reference well and said counter well.

7. An electrode structure as set forth in claim 2, wherein said electrolytic medium comprises a solid conductive polymer.

8. An electrode structure as set forth in claim 2, where said barrier comprises a gas pervious liquid impervious membrane.

9. A plurality of electrode structures as set forth in claim 5, wherein a sub-plurality of said plurality of electrode structures is sensitive to a single one of said selected species.

10. An electrode structure as set forth in claim 2, wherein said first well is a sensor well, said first well bottom is a sensor well bottom, said first passage is a sensor passage and said first electrode is a sensing electrode.

11. An electrode structure as set forth in claim 10, further including:
    a reference electrode in electrical communication with said electrolytic medium and electrically isolated from said sensing electrode other than via said electrolytic medium.

12. An electrode structure as set forth in claim 11, further including:
    electronic circuitry in said substrate adjacent said back surface adapted for processing signals from said sensing electrode and said reference electrode.

13. An electrode structure as set forth in claim 11, wherein:
    said substrate has a reference passage extending from said back surface to said sensor well bottom; and
    said reference electrode is wholly between said front and back surfaces of said substrate;
    and further including:
    a second conductor in said reference passage electrically communicating said reference electrode to adjacent said back surface.

14. A plurality of said electrode structures on said substrate, said plurality including a plurality of sensing electrodes and a plurality of reference electrodes as set forth in claim 13.

15. An electrode structure as set forth in claim 13, in combination with:
    a separate member having electronic circuitry adapted for processing signals from said sensing electrode and said reference electrode and means for connecting said first and second conductors to said electronic circuitry, 16. An electrode structure as set forth in claim 11, further including:
    a counter electrode in electrical communication with said electrolytic medium and electrically isolated from said sensing electrode and said reference electrode other than via said electrolytic medium.

17. An electrode structure as set forth in claim 16 wherein:
    said substrate has a reference passage extending from said back surface to said sensor well bottom; and
    said reference electrode is wholly between said front and back surfaces of said substrate;
    and further including:
    a second conductor in said reference passage electrically communicating said reference electrode to adjacent said back surface.

18. An electrode structure as set forth in claim 17, wherein:
    said substrate has a counter passage extending from said back surface to said sensor well bottom; and said counter electrode is wholly between said front and back surfaces of said substrate;
and further including:
a third conductor in said counter passage electrically communicating said counter electrode to adjacent said back surface.

19. A plurality of said electrode structures on said substrate, said plurality including a plurality of sensing electrodes and a plurality of counter electrodes as set forth in claim 18.

20. An electrode structure as set forth in claim 18, further including:
electronic circuitry in said substrate adjacent said back surface adapted for processing signals from said sensing electrode, said reference electrode and said counter electrode.

21. An electrode structure as set forth in claim 1, further including:
electronic circuitry in said substrate adjacent said back surface adapted for processing signals from said first electrode.

22. A plurality of electrode structures on said substrate, each of said electrode structures being as set forth in claim 1.

23. A plurality of electrode structures as set forth in claim 22, wherein a sub-plurality of said plurality of electrode structures is sensitive to a single one of said selected species.

24. A plurality of electrode structures as set forth in claim 22, said structures being arranged in adjacent relation and located along a straight line.

25. A plurality of electrode structures as set forth in claim 24, wherein said structures each have a width of no more than about 300 microns and said plurality has a length of no more than about 150 microns multiplied by the number of said structures.

26. A plurality of electrode structures as set forth in claim 24, further including:
one or more pressure sensors arranged in said straight line with said structures, 27. A plurality of electrode structures as set forth in claim 26, wherein said structures and said one or more pressure sensors each have a width of no more than about 300 microns and said plurality plus said one or more pressure sensor has a length of no more than about 150 microns multiplied by the number of said structures plus the number of said pressure sensors.

28. An electrode structure as set forth in claim 1, wherein said first well extends from about 40 to about 200 microns towards said back surface and wherein said back surface is from about 10 to about 100 microns from said first well bottom.

29. An electrode structure as set forth in claim 28 wherein said first well extends from about 60 to about 125 microns towards said back surface and wherein said back surface is from about 10 to about 40 microns from said first well bottom.

30. An electrode structure as set forth in claim 1, wherein said substrate is a semiconductor.

31. An electrode structure as set forth in claim 30, wherein said substrate is silicon, silicon carbide or gallium arsenide.

32. An electrode structure as set forth in claim 30, wherein said sensor well is formed by anisotropic etching and has sidewalls which form an obtuse angle with said front surface.

33. An electrode structure as set forth in claim 30, wherein said sensor well is formed by anisotropic etching and has sidewalls which form an obtuse angle with said front surface.

34. An electrode structure as set forth in claim 1, wherein said first electrode includes an electrode base and a conductive ion-selective member attached thereto and having an electroactive species incorporated therein.

35. An electrode structure as set forth in claim 34, wherein said first well extends sufficiently towards said back surface and said first electrode is sufficiently deeply positioned in said first well whereby electrochemical reaction of said moiety at said first electrode provides a substantially Nernstian slope.

36. An electrode structure as set forth in claim 34, further including:
electronic circuitry in said substrate adjacent said back surface adapted for processing signals from said first electrode.

37. An electrode structure as set forth in claim 34, wherein said substrate is silicon, silicon carbide or gallium arsenide.

38. A plurality of electrode structures on said substrate, said electrode structures being as set forth in claim 34.

39. An electrode structure as set forth in claim 34, wherein said substrate is a semiconductor.

40. An electrode structure as set forth in claim 34, wherein said first well extends from about 40 to about 200 microns towards said back surface and wherein said back surface is from about 10 to about 100 microns from said first well bottom.

41. An electrode structure as set forth in claim 34 wherein said first well extends from about 60 to about 125 microns towards said back surface and wherein said back surface is from about 10 to about 40 microns from said first well bottom.

42. An electrode structure as set forth in claim 34, wherein said first well is a sensor well, said first well bottom is a sensor well bottom, said first passage is a sensor passage, said first electrode is a sensing electrode and said first conductor is a sensor conductor.

43. An electrode structure as set forth in claim 42, wherein:
said substrate has a reference well extending into said substrate from said first surface towards said back surface and ending in a reference well bottom and a second passage extending from said back surface to said reference well bottom; and
a reference electrode in said reference well;
and further including:
a reference conductor in said second passage electrically communicating said reference electrode to adjacent said back surface.

44. An electrode structure as set forth in claim 43, wherein:
said substrate has a counter well extending into said substrate from said surface towards said back surface and ending in a counter well bottom and a third passage extending from said back surface to said counter well bottom; and
said counter electrode is in said counter and further including:
a counter conductor in said third passage electrically communicating said counter electrode to adjacent said back surface.

45. A plurality of said electrode structures on said substrate, said plurality including a plurality of sensing electrodes and a plurality of counter electrodes as set forth in claim 43.

46. An electrode structure as set forth in claim 42, further including:
   an electrolytic medium in contact with said sensing electrode; and
   a reference electrode in electrical communication with said electrolytic medium and electrically isolated from said sensing electrode other than via said electrolytic medium.

47. An electrode structure as set forth in claim 46, wherein said electrolytic medium comprises a solid conductor polymer.

48. An electrode structure as set forth in claim 46, further including:
   electronic circuitry in said substrate adjacent said back surface adapted for processing signals from said sensing electrode and said reference electrode.

49. An electrode structure as set forth in claim 46, wherein:
   said substrate has a second passage extending from said back surface to said sensor well bottom; and
   said reference electrode is in said sensor well;
   and further including:
   a reference conductor in said second passage electrically communicating said reference electrode to adjacent said back surface.

50. A plurality of said electrode structures on said substrate, said plurality including a plurality of sensing electrodes and a plurality of reference electrodes as set forth in claim 49.

51. An electrode structure as set forth in claim 46, further including:
   an electrolytic medium in contact with said sensing electrode; and
   a counter electrode in electrical communication with said electrolytic medium and electrically isolated from said sensing electrode and said reference electrode other than via said electrolytic medium.

52. An electrode structure as set forth in claim 51 wherein:
   said substrate has a second passage extending from said back surface to said sensor well bottom; and
   said reference electrode is in said sensor well;
   and further including:
   a reference conductor in said second passage electrically communicating said reference electrode to adjacent said back surface.

53. An electrode structure as set forth in claim 52, wherein:
   said substrate has a third passage extending from said back surface to said sensor well bottom; and
   said counter electrode is in said sensor well;
   and further including:
   a counter conductor in said third passage electrically communicating said counter electrode to adjacent said back surface.

54. An electrode structure as set forth in claim 53, further including:
   electronic circuitry in said substrate adjacent said back surface adapted for processing signals from said sensing electrode, said reference electrode and said counter electrode.

* * * * *